United States Patent
Wang et al.

(10) Patent No.: US 8,382,805 B2
(45) Date of Patent: Feb. 26, 2013

(54) BONE SCREW ASSEMBLY FOR LIMITED ANGULATION

(75) Inventors: Benjamin Wang, Carlsbad, CA (US); Srilakshmi Vishnubhotla, San Diego, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 380 days.

(21) Appl. No.: 12/792,072

(22) Filed: Jun. 2, 2010

(65) Prior Publication Data

US 2010/0305621 A1 Dec. 2, 2010

Related U.S. Application Data

(60) Provisional application No. 61/183,270, filed on Jun. 2, 2009.

(51) Int. Cl.
*A61B 17/70* (2006.01)
*A61B 17/86* (2006.01)

(52) U.S. Cl. .......................... 606/267; 606/306

(58) Field of Classification Search .......... 606/265–270, 606/300–301, 305–306
See application file for complete search history.

(56) References Cited

U.S. PATENT DOCUMENTS

| 8,002,806 B2 * | 8/2011 | Justis | 606/264 |
| 8,137,387 B2 * | 3/2012 | Garamszegi | 606/270 |
| 2006/0155277 A1 * | 7/2006 | Metz-Stavenhagen | 606/61 |
| 2009/0105770 A1 * | 4/2009 | Berrevoets et al. | 606/308 |
| 2009/0198280 A1 * | 8/2009 | Spratt et al. | 606/267 |

* cited by examiner

*Primary Examiner* — Kevin T Truong
*Assistant Examiner* — Larry E Waggle, Jr.
(74) *Attorney, Agent, or Firm* — Michael J. Loi

(57) ABSTRACT

A limited angulation bone screw assembly adapted to couple a spinal rod with a vertebra including a bone screw, a bushing and a housing. The pedicle screw having a shaft and an upper head portion, the upper head portion comprising a spherical surface with flats disposed on opposite sides of the upper head portion. The bushing comprising a lower rounded surface for mating with the spherical surface and flats of the upper head portion to restrict the angular movement of the bone screw. The coupled bone screw and bushing are inserted into the housing in a first orientation and then rotated to a second orientation to secure the coupled bone screw and bushing to complete the housing.

16 Claims, 6 Drawing Sheets

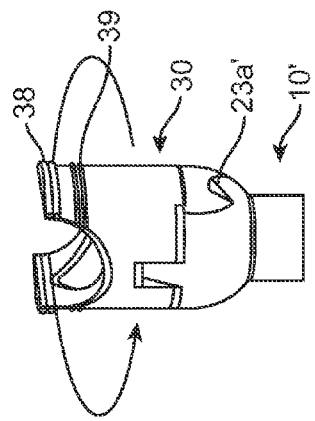
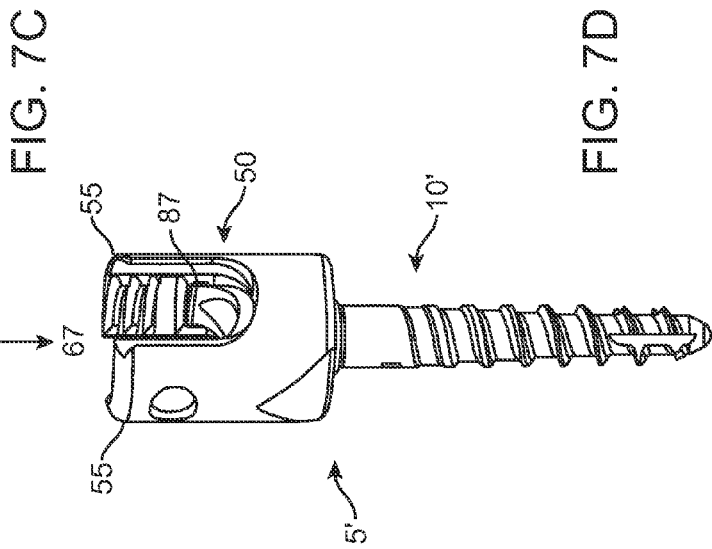
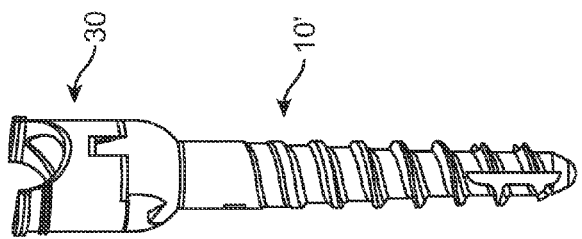
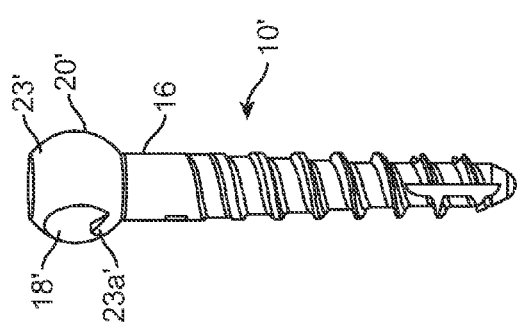
FIG. 7A
FIG. 7B
FIG. 7C
FIG. 7D

BONE SCREW ASSEMBLY FOR LIMITED ANGULATION

CROSS REFERENCE TO RELATED APPLICATIONS

This application claims the benefit of U.S. Provisional Application No. 61/183,270 filed Jun. 2, 2009, entitled "Bone Screw Assembly For Limited Angulation", the contents of which is incorporated herein by reference in its entirety.

BACKGROUND OF THE INVENTION

Field of the Invention

Embodiments of the present application are directed to a bone screw assembly for use in spinal surgery and in particular, to a bone screw assembly having restricted angular movement to a single plane.

Surgical intervention is often required to treat injuries and deformities of the spine. Scoliosis is one type of deformity of the spinal column having three components: coronal plane deformity, which is a side bending of the spine when viewed from the front or back; sagittal plane deformity, which is a loss of normal kyphotic curvature in the thoracic or chest area when viewed from the side; and axial plane deformity, which is a rotation of the spine around its own axis.

For rotational deformities of the spine, de-rotation maneuvers may need to be performed in-situ. Such de-rotation maneuvers place mechanical loads on the screw body in the sagittal plane, where resistance to lateral de-rotation forces is required to adequately correct the anatomy and restore alignment. It is therefore desirable to have bone screw assemblies suitable for de-rotation maneuvers, and preferably, for bone screw assemblies that allow for greater acceptance of rod deformities during construct.

SUMMARY

The bone screw assembly and methods described herein include a bone screw, a bushing and a housing. The pedicle screw having a shaft and an upper head portion, the upper head portion comprising a spherical surface with flats disposed on opposite sides of the upper head portion. The bushing comprising a lower rounded surface for mating with the spherical surface of the upper head portion and flanges coupled to the flats of the upper head portion to restrict the angular movement of the bone screw, preferably to a single plane. The coupled bone screw and bushing are inserted into the housing in a first orientation and then rotated to a second orientation to secure the coupled bone screw and bushing to complete the assembly.

In a first aspect, embodiments of the present invention provide a limited angulation bone screw assembly adapted to couple a spinal rod with a vertebra, the assembly including a bone screw comprising a threaded shaft and an upper head portion, the upper head portion being a substantially spherical surface having flat surfaces disposed on opposite sides of the upper head portion. A bushing comprising an upper portion having a seat shaped to receive the spinal rod and shoulders on both sides of the seat, and a lower portion having a rounded surface and a pair of opposing flanges having inner planar surfaces shaped to slidably couple with the spherical surface and flats of the bone screw to restrict motion of the bone screw to a single plane. A housing having an upper portion with a first opening, a lower portion with a second opening, and a first axis extending between the upper and lower portions, the upper portion comprising two spaced apart arms, each arm comprising internal threads and an internal groove configured to receive the shoulder of the bushing, and a U-shaped channel extending along a second axis transverse to the first axis adapted to receive the rod member, and the second opening being sized to engage the upper head portion of the bone screw. Wherein the screw is insertable through the first opening until the threaded shaft extends through the second opening and the upper head portion engages the second opening and the bushing is insertable through the first opening in a first orientation with the shoulders being positioned between the spaced apart arms until the shoulders are proximate the internal grooves, the bushing then being rotateable to a second orientation with the shoulders being inserted into the internal grooves and the bushing seat aligning with the U-shaped channel and the upper head portion of the screw couples with the lower portion of the bushing and permits angulation of the housing relative to the bone screw in a plane including the first and second axis.

In another aspect, embodiments of the present invention provide a limited angulation bone screw assembly having a bone screw comprising a shaft and a substantially spherical upper head portion having flat surfaces disposed on opposite sides of the upper head portion, a bushing having an upper portion and a lower portion, the lower portion configured to mate with the upper head portion and the flat surfaces of the bone screw to restrict motion of the bone screw to a single plane and the upper portion having a seat shaped to receive the spinal rod and shoulders on both sides of the seat, and a housing having an upper portion, a lower portion and a first axis extending between the upper and lower portions, the housing having a first opening at the upper portion, a second opening at the lower portion and internal grooves configured to receive the shoulders of the bushing. Wherein the mated bushing and screw are insertable through the first opening in a first orientation until the shaft extends through the second opening and the shoulders are proximate the internal grooves, the bushing and screw then being rotateable to a second orientation with the shoulders being inserted into the internal grooves, and the seat aligns with the upper portion of the housing to receive a spinal rod therein along a second axis transverse to the first axis.

In many embodiments, the bushing may have a groove adjacent the shoulder. In some embodiments the housing may include one or more protruding members configured to mate with the groove. In other embodiments, the groove may provide frictional engagement with the housing.

In many embodiments, the lower portion of the bushing further includes cut-away portions formed along a bottom circumferential surface. In some embodiments the cut-away portions are configured to splay over the upper head portion of the screw when the bushing is in a crush locked position.

In many embodiments, the bone screw assembly further includes a set screw having external threads configured to engage the internal threads of the housing.

In many embodiments, the upper portion further comprising a recess configured to interface with an instrument interface.

In another aspect, embodiments of the present invention provide a method of assembling a bone screw assembly capable of uniplanar movement is provided, the method including a bone screw, the bone screw having a spherical surface adjacent first planar surfaces; providing a bushing, the bushing comprising flanges having second planar surfaces; coupling the first planar surfaces of the bone screw with the second planar surfaces of the bushing to restrict movement of the bone screw to a single plane; providing a housing and delivering the coupled bone screw and bushing into the housing; and rotating the coupled bone screw and bushing to secure the coupled bone screw and bushing to the housing.

BRIEF DESCRIPTION OF THE DRAWINGS

FIGS. 7A-7D are perspective views of another embodiment of a bone screw assembly in various stages of assembly.

DETAILED DESCRIPTION OF THE EMBODIMENTS

Embodiments of the present application are directed to a bone screw assembly and in particular, to a bone screw assembly capable of having restricted angular movement, such as movement that is restricted to a single plane. In some embodiments, the bone screw assembly can be used in spinal surgery, such as in pedicles. In some embodiments, the bone screw assembly can be inserted into the sacrum or the iliac. The bone screw assembly is adapted to receive a rod or other rigid member and to secure the rod to one or more vertebra. In some embodiments, the bone screw assembly includes a bone screw having an angulation relative to a housing that is restricted in one directions or planes. As used herein "angulation" describes the ability or lack thereof of the screw being positionable in a range of positions in which a range of angles is formed between the screw and the housing. In a preferred embodiment, the bone screw assembly includes a bone screw having movement restricted to only in a single plane. Such a screw is capable of providing angulation only in that plane.

In some embodiments, the screw assemblies described herein comprise lightweight, low profile bone screw assembly that are constructed to allow each component thereof to secure other pieces within the overall structure to minimize the risk of disassembly when in use.

In some embodiments, a bone screw assembly 5 comprises a bone screw 10, a bushing 30 and a housing 50 (shown in FIGS. 1-4). According to some embodiments, when all the components are fully assembled, the bone screw 10 can pivot and achieve various angles relative to another component of the screw (e.g., the housing as discussed below) only along a single plane. In a preferred embodiment, the bone screw 10 is assembled and placed in a patient such that the bone screw 10 pivots or angulates only along a cephalad-caudal plane. Preferably, the bone screw assembly allows the housing 50 to angulate cephalad-caudally to accept a rod, but resists movement (e.g., is rigid) in the medial-lateral plane to allow for the transferring of de-rotation forces to vertebral movement. In contrast, polyaxial screws would respond to such forces by being deflected. Thus, this application describes bone screw assemblies that combine the force transferring advantages of a monoaxial fixed screw head with the variable head positioning of a polyaxial screw. An additional benefit of having a bone screw 10 that is restricted to angulation only along a cephalad-caudal plane is that this allows for greater acceptance of deformity rods during spinal surgeries.

Figure 1:
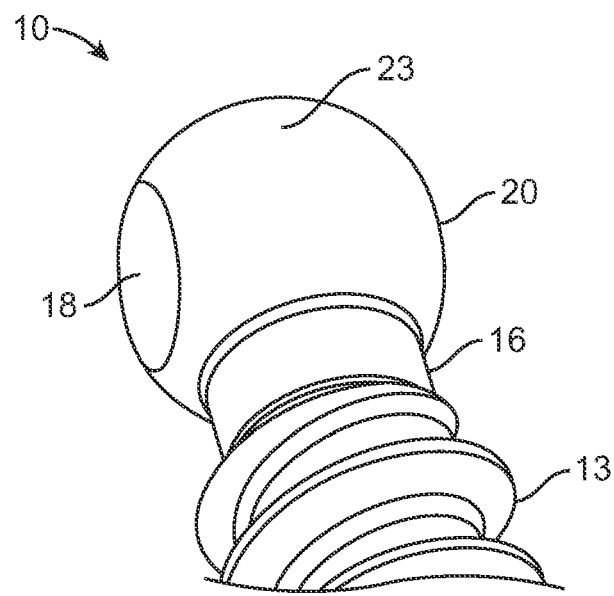
FIG. 1 is a perspective view of a bone screw according to some embodiments of the present application.

FIG. 1 illustrates a bone screw 10 according to some embodiments of the present application. The bone screw 10 comprises a threaded shaft 13, a neck 16, and an upper head portion 20 attached to the threaded shaft 13 by the neck 16. The shaft 13 is elongate and has a lower body ending in a tip (shown in FIGS. 5A-5C) that is implantable into a bone. The threaded shaft 13 includes a number of helical threads extending radially outward from and along at least a portion of the length of the shaft. The neck 16 comprises a cylindrically shaped portion that is located between and connects the threaded shaft 13 to the upper head portion 20.

The upper head portion 20 comprises a spherical surface 23 adjacent a plurality of flat surfaces or flats 18. In some embodiments, the flats 18 comprise a circular or an oval region of the head. In other embodiments, non-flat surfaces capable of coupling with other surfaces of a screw assembly to limit angulation are adjacent spherical surface 23. As shown in FIG. 1, in some embodiments, the upper head portion 20 comprises two flats 18 that are disposed on opposite sides of the spherical surface 23. The flats 18 can be symmetrical at least in part. In other embodiments, a single flat or more than two flats (e.g., three or four), can be provided on the upper head portion 20. As described in more detail below, the flats 18 cooperate with other surfaces of a screw assembly to limit angulation, such as by coupling with corresponding surfaces. In various embodiments described below, the flats 18 are configured to couple with extended flanges 43 of the bushing 30.

Figure 2:
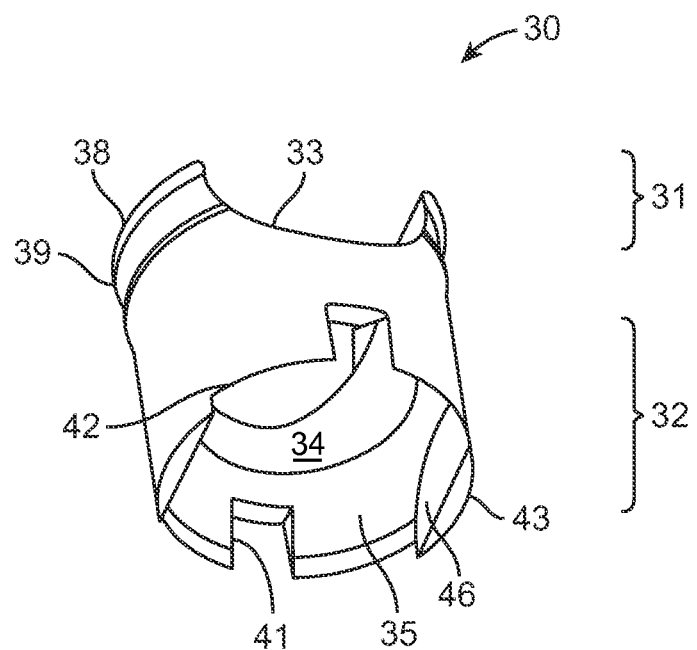
FIG. 2 is a perspective view of a bushing according to some embodiments of the present application.

FIG. 2 illustrates the bushing 30 according to some embodiments of the present application. The bushing 30 comprises an upper portion 31, a lower portion 32, and an axial bore 34 running therethrough. The upper portion 31 comprises a surface or seat 33 for receiving a rod member. The seat 33 can be shaped to form a portion of a U-shaped channel, as discussed further below. The upper portion 31 of the bushing 30 also includes a shoulder 38 adjacent a groove 39. In some embodiments, the shoulder 38 allows one or more instruments to easily grasp and secure the bushing 30. In some embodiments, the shoulder 38 serves to prevent disassembly after the bushing 30 is inserted into a housing member 50 by sliding or snapping into a corresponding groove inside the housing member 50 (shown best in FIGS. 6A and 6B) to prevent the bushing 30 from backing out of assembly. The groove 39, adjacent the shoulder 38, forms a track around the top surface of the bushing 30. In some embodiments, one or more protruding members of the housing can mate with the bushing 30 by slideably engaging in the groove 39. In some embodiments, the groove 39 of the bushing 30 helps to prevent migration of the bushing 30 in the housing 50. In some embodiments, the groove 39 adds friction between the bushing 30 and the housing 50 to help lock the angulation of the bone screw 10 in place after the bushing 30 is crush-locked into place with the bone screw 10 by a set screw as discussed below. While FIG. 2 illustrates the groove 39 extending along the entire top surface of the bushing 30, in some embodiments, the groove 39 is formed only along a portion of the top surface of the bushing 30. In some embodiments, the groove is formed on the top surface of the bushing 30 on both sides of the U-shaped channel, as shown in FIG. 2.

The lower portion 32 of the bushing 30 comprises a lower rounded surface 35 in the interior of the bushing 30 and a plurality of flanges 43 that extend below the bottom circumferential surface 42. The lower portion 32 can also include cut-away portions 41 formed along the bottom circumferential surface 42 of the bushing in some embodiments.

The lower portion 32 of the bushing 30 includes lower rounded surface 35 located in the interior of the bushing 30. The lower rounded surface 35 surrounds axial bore 34 and is shaped to mate or couple with the spherical surface 23 of the bone screw 10 when the bushing 30 is brought into contact with the bone screw 10.

The lower portion 32 of the bushing 30 also includes one or more flanges 43 that extend below bottom circumferential surface 42. As shown in FIG. 2, in some embodiments, the flanges 43 comprise flat or planar surfaces 46 that face inwardly (toward the axis 34). The planar surfaces 46 are constructed to mate or couple with at least a portion of the surfaces of the flats 18 to assist in coupling the bushing 30 to the bone screw 10. In some embodiments, when coupled with the flats 18 of the bone screw 10, the planar surfaces 46 of the flanges 43 restrict the angular movement of the bone screw 10 relative to the housing 50. In a preferred embodiment, when coupled with the flats 18 of the bone screw 10, the planar surfaces 46 of the flanges 43 restrict the angular movement of the housing to a single plane relative to the bone screw 10 when the bone screw is in a fixed position (e.g., when anchored in a vertebra). For example, a frictional engagement of the flanges 43 with the flats 18 could enable the housing 50 to remain in a selected position relative to the screw 10. In other embodiments, the inner surfaces of the flanges 43 need not be planar, but can be of any suitable non-planar shape capable of coupling with the bone screw head 10 to restrict the motion thereof, e.g., in a uniplanar manner.

While in some embodiments the flanges 43 are rigid members, in other embodiments, the flanges 43 are relatively flexible members that are capable of some degree of splaying when placed in contact with a portion of the upper head portion 20 of the bone screw 10. Splaying provides the advantage of allowing the flanges 43 to provide a compressive force on the flats 18 when the bushing 30 is coupled to the bone screw 10, thereby assisting in keeping the bushing 30 snug with the upper head portion 20 of the bone screw 10. In some embodiments, the flanges 43 apply a compressive force against the flats 18 of the bone screw 10 to couple the two components together after providing and tightening a set screw as described below.

In some embodiments, the lower portion 32 of the bushing 30 also includes cut-away portions 41 formed along the bottom circumferential surface 42 of the bushing 30. The cut-away portions 41 serve as notches that allow for effective crushing of the bushing 30 over the upper head portion 20 of the bone screw 10 when a set screw is tightened. In some embodiments, the cut-away portions 41 allows splaying of the lower portion of the bushing 30 around the upper head portion 20 of the bone screw 10 when the bushing 30 is crush locked into position with the bone screw 10 by tightening of a set screw.

Figure 3:
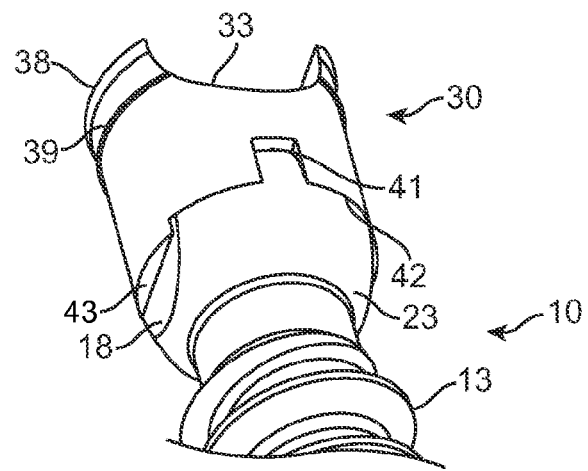
FIG. 3 is a perspective view of a bone screw coupled with a bushing according to some embodiments of the present application.

FIG. 3 illustrates a perspective view of a bone screw 10 coupled with a bushing 30 according to embodiments of the present application. The inner planar surfaces 46 of the bushing 30 extend downwardly adjacent to, and, in some cases in contact with, the flats 18 of the bone screw 10. In some cases, the planar surfaces 46 provide a coupling between the bushing 30 and the bone screw 10. As shown in FIG. 3, in some embodiments, when the bushing 30 is coupled with the bone screw 10, the planar surfaces 46 of the flanges 43 contact a portion of the surface area of the flats 18. While in some embodiments, the planar surfaces 46 of the flanges 43 contact a minimal portion of the surface area of the flats 18 (e.g., less than 50% of the surface area), in other embodiments, the planar surfaces 46 of the flanges 43 contact a majority of the surface area of the flats 18, as shown in FIG. 3.

Figures 4A, 4B:
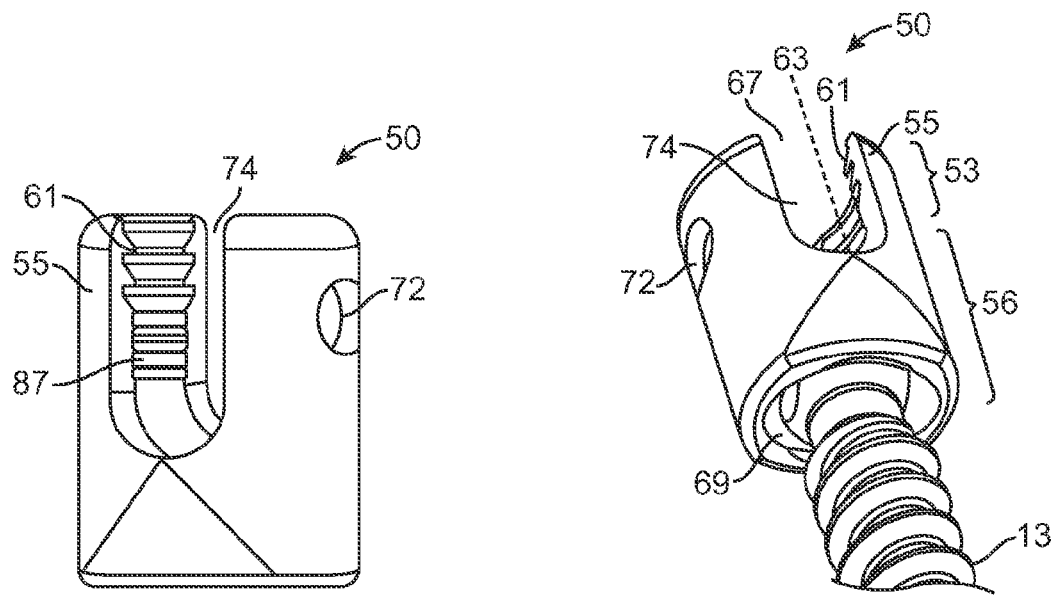
FIG. 4A is a perspective view of a housing according to some embodiments of the present application.
FIG. 4B is a perspective view of a housing with a bone screw inserted therein according to some embodiments of the present application.

FIG. 4A illustrates a perspective view of a housing 50 according to some embodiments of the present application, while FIG. 4B illustrates a perspective view of the housing 50 with a bone screw 10 received therein. The housing 50 is a cylindrically shaped member in some embodiments that comprises an upper portion 53, a lower portion 56, and a first axis 63 extending between the upper and lower portions. In some embodiments, the upper portion 53 comprises two spaced apart upstanding arms 55 defining, at least in part, a U-shaped channel 74 extending along a second axis transverse to the first axis 63. Each of the arms 55 contains internal threads 61. In some embodiments, the internal threads 61 comprise helical structures capable of interlocking with complementary surfaces as found for example in U.S. Pat. No. 6,726,689 to Jackson, filed Sep. 6, 2009, and herein incorporated by reference in its entirety and included in an appendix below. The top of the arms 55 form the first opening 67 at the top of the housing 50. The arms 55 are disposed on opposite sides of the axis 63 and can be shaped similarly (e.g., minor images of each other), although in some embodiments, one arm can be sized or shaped differently from another. The upper portion 53 of the housing also includes a hole, opening, or recess 72 for receiving a protruding member of an instrument (e.g. a sleeve or rod reducer).

Figure 6A:
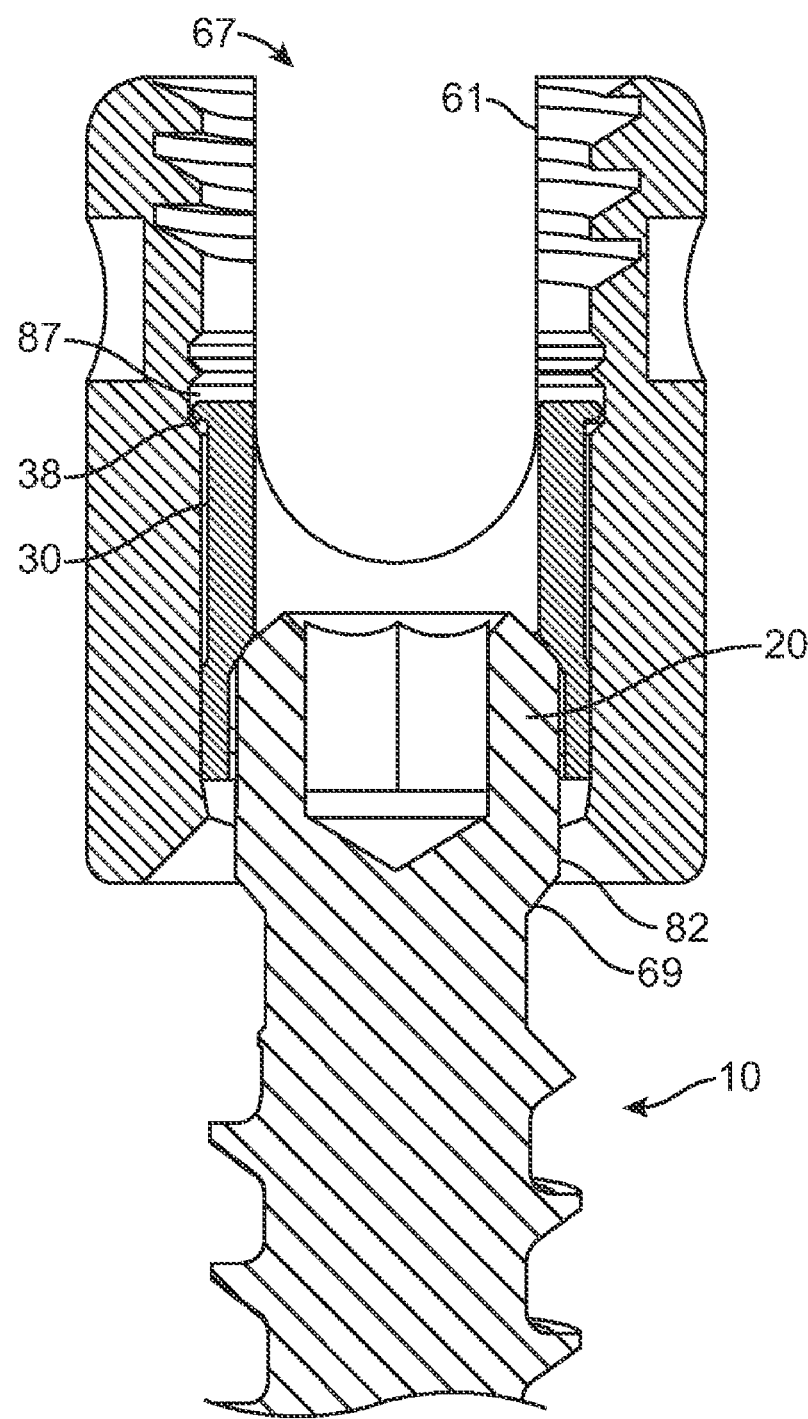
FIGS. 6A-6B are cross-sectional views of a bone screw assembly according to some embodiments of the present application.
Figure 6B:
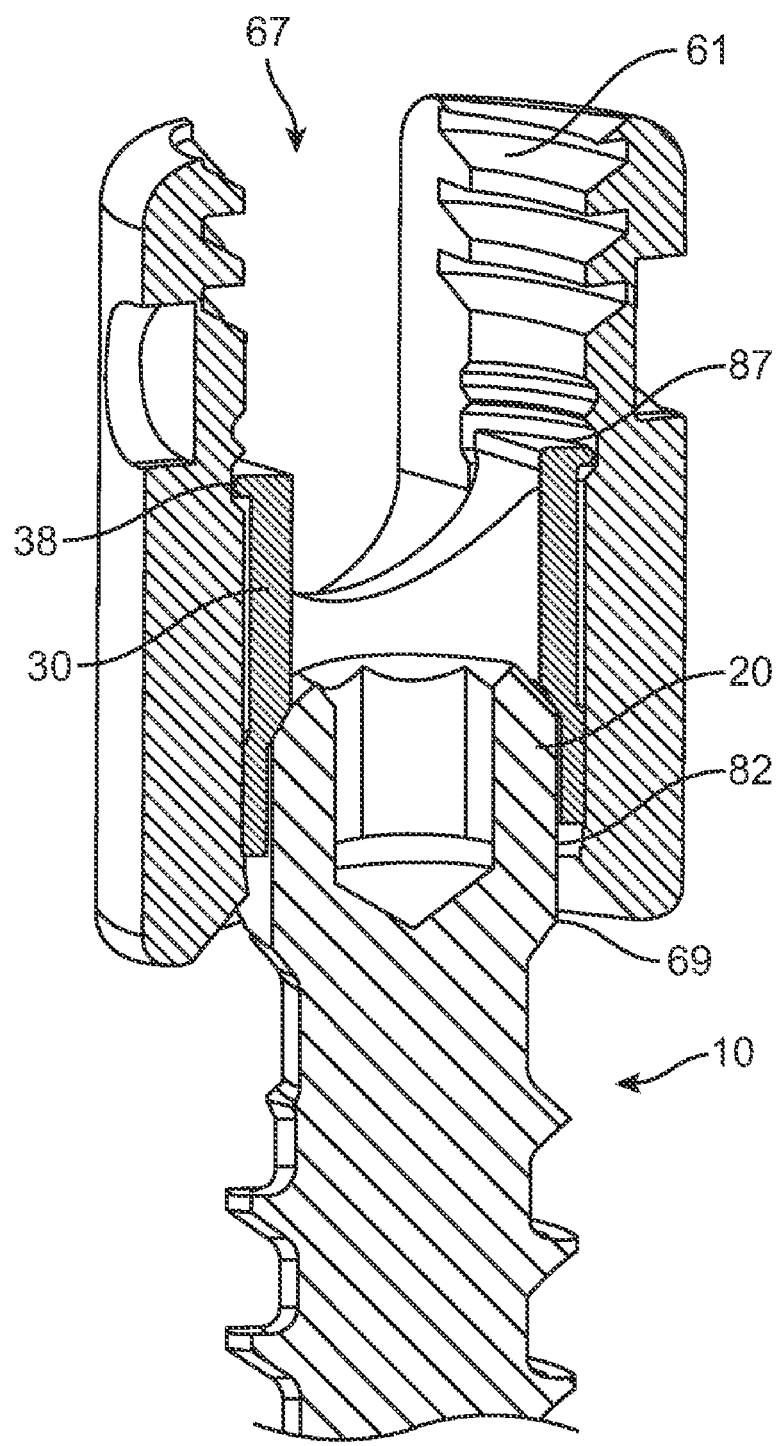

The lower portion 56 of the housing 50 comprises a second opening 69 through which at least a portion of the bone screw 10 extends. For example, as illustrated in FIG. 4B, during assembly, the bone screw 10 passes through the second opening 69 such that at least a portion of the upper head portion 20 of the bone screw 10 is retained in the interior of the housing 50, while at least a portion of the threaded shaft 13 is disposed outside of the housing 50. To retain the coupled bone screw 10 and bushing 30 in the housing 50, in some embodiments, the housing 50 includes internal protrusions (not shown) that can slideably engage the grooves 39 of the bushing 30 upon drop loading, press fitting and rotation of the bushing 30 in the housing 50. In other embodiments, to retain the coupled bone screw 10 and bushing 30 in the housing, the housing 50 includes an internal groove 87 that receives the shoulder 38 of the bushing 30 (as shown in FIGS. 6A and 6B) to secure the assembly.

Figure 5A:
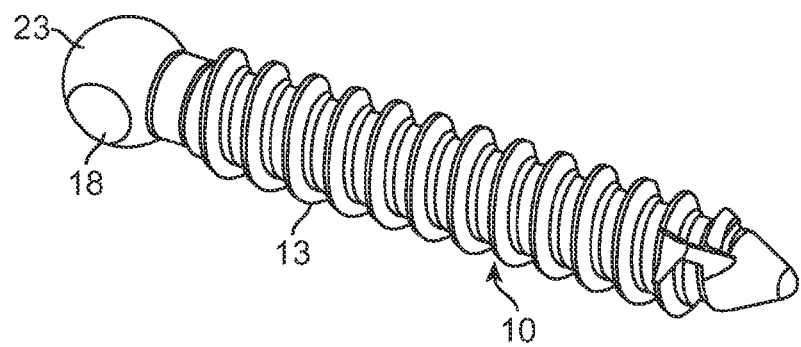
FIGS. 5A-5C are side perspective views of a bone screw assembly in various stages of assembly according to some embodiments.
Figure 5B:
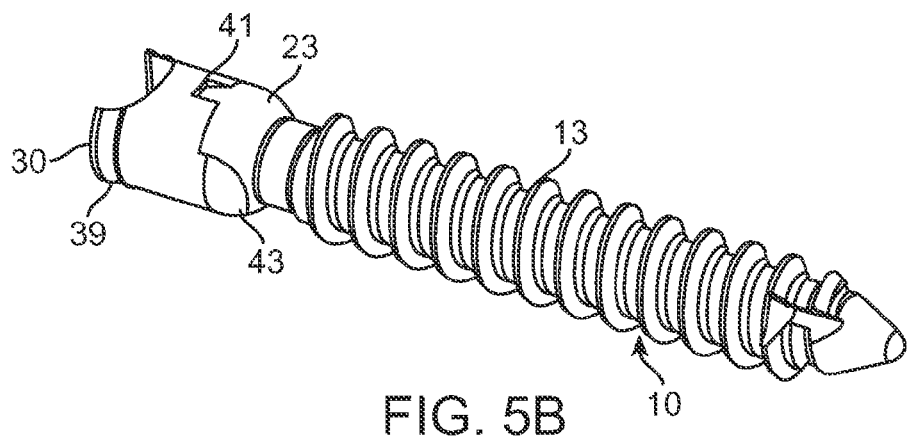
Figure 5C:
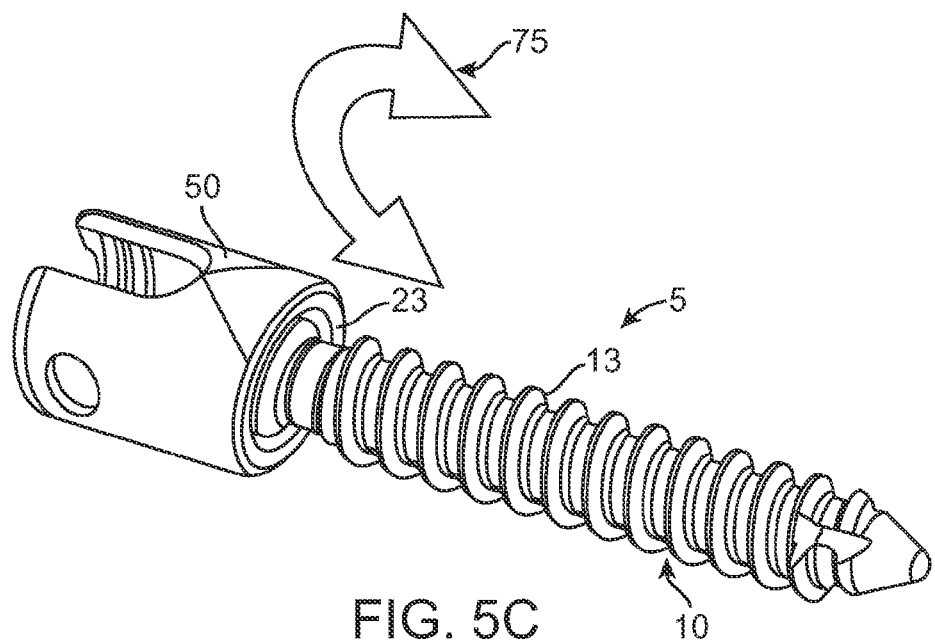

FIGS. 5A-5C illustrate various stages of assembly of the bone screw assembly 5 according to some embodiments of the present application. Methods of assembly can comprise providing a bone screw 10, inserting the bone screw 10 into a housing 50, coupling the bone screw 10 with a bushing 30, and rotating the bushing 30 within the housing 50.

As shown in FIG. 5A, a bone screw 10 is provided. In some embodiments, the bone screw 10 can comprise an upper head portion 20 that is at least partially separate from the threaded shaft 13, and which may therefore need to be assembled. However, as shown in FIG. 5A, the bone screw 10 comprises a threaded shaft 13 already attached to the head portion 20 by a neck 16. In some embodiments, the threaded shaft 13 and upper head portion 20 are formed from a monolithic piece. In some embodiments, the bone screw 10 is drop-loaded downwardly (e.g., top-loaded) into the first opening 67 of the housing 50 before the bushing 30 is coupled with the bone screw 10. The second opening 69 of the housing 50 is sized smaller than the diameter of the top portion 20 of the bone screw 10 such that the bone screw 10 can be drop-loaded into the housing 50 so that the bone screw 10 rests within the housing 50. As shown in FIGS. 6A and 6B, a bottom surface of the upper head portion 20 can abut internal walls 82 of the housing 50.

After the bone screw 10 is drop-loaded into the housing 50, the bushing 30 can be drop-loaded downwardly (e.g., top-loaded) into the housing 50 to couple with the bone screw 10. An illustration of a coupled bushing 30 and bone screw 10 is shown in FIG. 5B. In some embodiments, to couple the bushing 30 with the bone screw 10, the bushing 30 can be press-fitted into contact with at least the partial spherical surface 23 of the bone screw 10. Such insertion can cause the lower rounded surface 35 of the bushing 30 to engage the surface 23. In this position, the flanges 43 can be disposed adjacent to or directly couple with the flats 18 of the bone screw 10.

To drop-load the bushing 30 into the housing 50, the bushing 30 should be about 90 degrees offset from its final assembly position to allow the bushing 30 to clear the internal threads 61 of the housing 50 (shown in FIGS. 6A-6B). Once the bushing 30 rests on the bone screw 10, the bushing can be rotated within the housing 50 to secure the bushing 30 to the housing 50. For example, the bushing 30 can be rotated within the housing 50 such that the shoulder 38 of the bushing 30 rests within an internal groove 87 of the housing 50, thereby securing the components together. In some embodiments, the coupled bone screw 10 and bushing 30 are rotated between 1 and 90 degrees, while in other embodiment, these components are rotated between 30 and 90 degrees, within the housing 50 to ensure that the internal protrusions within the housing 50 are slideably engaged in the grooves 39 of the bushing 30.

When fully assembled, the bone screw 10, bushing 30 and housing 50 form a bone screw assembly capable of angulation in a limited number of planes. In some embodiments, even after the bushing 30 is press-fitted with the bone screw 10 and rotated into place in the housing 50, the bushing 30 rests loosely inside the housing 50 and allows for polyaxial freedom of movement. In a preferred embodiment, the bone screw assembly restricts angulation of the bone screw to a single plane. Arrow 75 (shown in FIG. 5C) illustrates the direction of rotation or pivoting of the bone screw 10 relative to the housing 50. As shown, bone screw 10 is capable of angular movement only along a single plane, e.g., the direction indicated by the arrow 75. In some embodiments, the bone screw 10 of the bone screw assembly 5 can pivot or angulate between 0 and nearly 90 degrees in a single plane. For example, the bone screw 10 can pivot or angulate between +/−45 degrees from the axis 63.

Following assembly of the bone screw 10, bushing 30 and housing 50, an implant or rod member (not shown) can be delivered down the housing 50 and past the internal threads 61 and rest on top of the top portion 20 of the bone screw 10. After delivering the rod member, a cap or set screw (not shown) can be delivered downwardly through the housing 50. The set screw comprises external threads that mate with the internal threads 61 of the housing 50. The set screw can apply a downward tightening or compression force on the rod member. The compression force is translated to the bushing 30, and the bushing 30 is deformed within the housing 50 (sometimes referred to herein as being "crushed" or "crush-locked") into more complete contact with the bone screw 10, thereby locking the bone screw 30 at a fixed angle with respect to the housing 50.

FIGS. 7A-7D illustrate another embodiment of a bone screw assembly 5'. Methods of assembly can comprise providing a bone screw 10', inserting the bone screw 10' into a housing 50, coupling the bone screw 10' with a bushing 30, and rotating the bushing 30 within the housing 50.

FIG. 7A illustrates a bone screw 10' according to some embodiments of the present application. The bone screw 10' comprises a threaded shaft 13, a neck 16, and an upper head portion 20' attached to the threaded shaft 13 by the neck 16. The shaft 13 is elongate and has a lower body ending in a tip that is implantable into a bone. The threaded shaft 13 includes a number of helical threads extending radially outward from and along at least a portion of the length of the shaft. The neck 16 comprises a cylindrically shaped portion that is located between and connects the threaded shaft 13 to the upper head portion 20'.

The upper head portion 20' comprises a spherical surface 23' adjacent flat surfaces or flats 18' that are disposed on opposite sides of the spherical surface 23'. Flats 18' are similar to flats 18 described above except flats 18' do not form a circular or an oval region of the head portion 20'. Instead, a portion of the spherical surface or protrusion 23a' extends outside of the flats 18' below the bushing engagement area to add lateral support in medial-lateral bending loading modes (such as derotation) by leaving material on the spherical tip.

Similar to the embodiments disclosed above, the flats 18' cooperate with other surfaces of a screw assembly to limit angulation, such as by coupling with corresponding surfaces of the bushing 30 and housing 50. In addition, portions or protrusion 23a' also interact with the bushing 30 and housing 50 to increase resistance off-axis angulation of the screw 10'.

In some embodiments, the bone screw 10' is drop-loaded downwardly (e.g., top-loaded) into the first opening 67 of the housing 50 before the bushing 30 is coupled with the bone screw 10. The second opening 69 of the housing 50 is sized smaller than the diameter of the top portion 20 of the bone screw 10' such that the bone screw 10' can be drop-loaded into the housing 50 so that the bone screw 10' rests within the housing 50.

After the bone screw 10' is drop-loaded into the housing 50, the bushing 30 can be drop-loaded downwardly (e.g., top-loaded) into the housing 50 to couple with the bone screw 10.

In some embodiments, to couple the bushing 30 with the bone screw 10', the bushing 30 can be press-fitted into contact with at least the partial spherical surface 23' of the bone screw 10', shown in FIG. 7B. Such insertion can cause the lower rounded surface 35 of the bushing 30 to engage the surface 23'. In this position, the flanges 43 can be disposed adjacent to or directly couple with the flats 18' of the bone screw 10'.

To drop-load the bushing 30 into the housing 50, the bushing 30 should be rotated about 90 degrees offset from its final assembly position, first orientation, to allow the bushing 30 to clear the internal threads 61 of the housing 50 (shown in FIG. 7C). Once the bushing 30 shoulders 38 are proximate the internal grooves 87, the bushing can be rotated within the housing 50 to a second orientation to secure the bushing 30 to the housing 50. For example, the bushing 30 can be rotated within the housing 50 such that the shoulder 38 of the bushing 30 rests within an internal groove 87 of the housing 50, thereby securing the components together. In some embodiments, the coupled bone screw 10 and bushing 30 are rotated between 1 and 90 degrees, while in other embodiment, these components are rotated between 30 and 90 degrees, within the housing 50 to ensure that the internal protrusions within the housing 50 are slideably engaged in the grooves 39 of the bushing 30.

When fully assembled, the bone screw 10', bushing 30 and housing 50 form a bone screw assembly 5' capable of angulation in a limited number of planes, shown in FIG. 7D. In some embodiments, even after the bushing 30 is press-fitted with the bone screw 10 and rotated into place in the housing 50, the bushing 30 rests loosely inside the housing 50 and allows for uniaxial freedom of movement. In a preferred embodiment, the bone screw assembly restricts angulation of the bone screw to a single plane. In some embodiments, the bone screw 10' of the bone screw assembly 5' can pivot or angulate between 0 and nearly 90 degrees, or between 10 and 80 degrees, in a single plane. For example, the bone screw 10 can pivot or angulate between +/−45 degrees from the axis 63.

Following assembly of the bone screw 10', bushing 30 and housing 50, an implant or rod member (not shown) can be delivered down the housing 50 and past the internal threads 61 and rest on top of the top portion 20' of the bone screw 10'. After delivering the rod member, a cap or set screw (not shown) can be delivered downwardly through the housing 50. The set screw comprises external threads that mate with the internal threads 61 of the housing 50. The set screw can apply a downward tightening or compression force on the rod member. The compression force is translated to the bushing 30, and the bushing 30 is deformed within the housing 50 (sometimes referred to herein as being "crushed" or "crush-locked") into more complete contact with the bone screw 10', thereby locking the bone screw 10' at a fixed angle with respect to the housing 50.

It will be apparent to those skilled in the art that various modifications and variations can be made in the present invention without departing from the scope or spirit of the invention. Thus, it is intended that the present invention cover the modifications and variations of this invention provided that they come within the scope of the appended claims or their equivalents.

What is claimed is:

1. A limited angulation bone screw assembly adapted to couple a spinal rod with a vertebra, comprising:
    a bone screw (10) comprising a threaded shaft (13) and an upper head portion (20), the upper head portion (20) being a substantially spherical surface (23) having flat surfaces (18) disposed on opposite sides of the upper head portion (20);
    a bushing (30) comprising an upper portion (31) having a seat (33) shaped to receive the spinal rod and shoulders (38) on both sides of the seat, and a lower portion (32) having a rounded surface (35) and a pair of opposing flanges (43) having inner planar surfaces (46) shaped to slidably couple with the spherical surface (23) and flat surfaces (18) of the bone screw (10) to restrict motion of the bone screw to a single plane; and
    a housing (50) having an upper portion (53) with a first opening (67), a lower portion (56) with a second opening (69), and a first axis (63) extending between the upper and lower portions, the upper portion (53) comprising two spaced apart arms (55), each arm comprising internal threads (61) and an internal groove (87) configured to receive the shoulder (38) of the bushing (30), and a U-shaped channel (74) extending along a second axis transverse to the first axis (63) adapted to receive the spinal rod, and the second opening (69) being sized to engage the upper head portion (20) of the bone screw (10);
    wherein the screw is insertable through the first opening (67) until the threaded shaft (13) extends through the second opening (69) and the upper head portion (20) engages the second opening (69);
    wherein the bushing (30) is insertable through the first opening (67) in a first orientation with the shoulders (38) being positioned between the spaced apart arms (55) until the shoulders (38) are proximate to the internal grooves (87), the bushing (30) then being rotateable to a second orientation with the shoulders (38) being inserted into the internal grooves (87) and the bushing seat (33) aligning with the U-shaped channel (74); and
    wherein the upper head portion (20) of the screw couples with the lower portion (32) of the bushing (30) and permits angulation of the housing (50) relative to the bone screw (10) in a plane including the first and second axis,
    wherein the bushing (30) further comprises a groove (39) adjacent the shoulder (38) for frictional engagement with the housing.

2. The bone screw assembly of claim 1, wherein the housing further includes one or more protruding members configured to mate with the groove (39).

3. The bone screw assembly of claim 1, wherein prior to insertion through the first opening (67), the upper head portion (20) of the screw (10) is engaged with the lower portion (32) of the bushing (30) in the first orientation, and after insertion of both the bushing (30) and screw (10) when the shoulders (38) are proximate the internal grooves (87), both the bushing (30) and screw (10) are rotated to the second orientation.

4. The bone screw assembly of claim 1, wherein the lower portion (32) of the bushing (30) further includes cut-away portions (41) formed along a bottom circumferential surface (42).

5. The bone screw assembly of claim 4, wherein the cut-away portions (41) are configured to splay over the upper head portion (20) of the screw (10) when the bushing (30) is in a crush locked position.

6. The bone screw assembly of claim 1, wherein the flat surfaces (18) includes protrusions (23a').

7. The bone screw assembly of claim 1, further comprising a set screw having external threads configured to engage the internal threads (61) of the housing (50).

8. The bone screw assembly of claim 1, wherein the upper portion (53) further comprising a recess (72) configured to interface with an instrument interface.

9. A limited angulation bone screw assembly, comprising:
    a bone screw comprising a shaft and a substantially spherical upper head portion having flat surfaces disposed on opposite sides of the upper head portion;
    a bushing having an upper portion and a lower portion, the lower portion configured to mate with the upper head portion and the flat surfaces of the bone screw to restrict motion of the bone screw to a single plane and the upper portion having a seat shaped to receive a spinal rod and shoulders on both sides of the seat; and
    a housing having an upper portion, a lower portion and a first axis extending between the upper and lower portions, the housing having a first opening at the upper portion, a second opening at the lower portion and internal grooves configured to receive the shoulders of the bushing;
    wherein the mated bushing and screw are insertable through the first opening in a first orientation until the shaft extends through the second opening and the shoulders are proximate the internal grooves, the bushing and screw then being rotateable to a second orientation with the shoulders being inserted into the internal grooves, and
    wherein the seat aligns with the upper portion of the housing to receive a spinal rod therein along a second axis transverse to the first axis, wherein the bushing further comprises a groove adjacent the shoulder configured for frictional engagement with the housing.

10. The bone screw assembly of claim 9, wherein the bushing further comprises a groove adjacent the shoulder and the housing further includes one or more protruding members configured to mate with the groove.

11. The bone screw assembly of claim 9, wherein the lower portion of the bushing further includes cut-away portions formed along a bottom circumferential surface, the cut-away portions being configured to splay over the upper head portion of the screw when the bushing is in a crush locked position.

12. The bone screw assembly of claim 9, wherein the flat surfaces includes protrusions.

13. The bone screw assembly of claim 9, further comprising a set screw having external threads configured to engage internal threads within the housing.

14. The bone screw assembly of claim 9, wherein the upper portion further comprising a recess configured to interface with an instrument interface.

15. A method of assembling a bone screw assembly capable of uniplanar movement, comprising:
  providing a bone screw comprising a shaft and an upper head portion, the upper head portion comprising a spherical surface adjacent first planar surfaces;
  providing a bushing, the bushing comprising an upper portion and a lower portion, the upper portion comprising a groove, the lower portion defining a lower rounded surface, the lower portion further comprising flanges having second planar surfaces;
  coupling first planar surfaces of the bone screw with second planar surfaces of the bushing to thereby restrict movement of the bone screw to a single plane;
  providing a housing having an upper portion, a lower portion and a first axis extending between the upper and lower portions, the housing having a first opening at the upper portion and a second opening at the lower portion, the housing further comprising an inner groove for receiving the shoulder of the bushing;
  delivering the bone screw and bushing into the housing; and
  rotating the bushing until the shoulder of the bushing is received in a groove of the housing,
  wherein delivering comprises drop-loading the bone screw downwardly into the housing, followed by drop-loading the bushing into the housing on top of the bone screw.

16. The method of claim 15, wherein delivering comprises drop-loading the bone screw and bushing downwardly together into the housing.

* * * * *